United States Patent [19]

Crawford

[11] Patent Number: 5,046,003
[45] Date of Patent: Sep. 3, 1991

[54] METHOD FOR REDUCING SKEW IMAGE ARTIFACTS IN HELICAL PROJECTION IMAGING

[75] Inventor: Carl R. Crawford, Milwaukee, Wis.

[73] Assignee: General Electric Company, Milwaukee, Wis.

[21] Appl. No.: 371,332

[22] Filed: Jun. 26, 1989

[51] Int. Cl.$^5$ .................. G06F 15/42; G06F 15/64
[52] U.S. Cl. ...................... 364/413.15; 364/413.21; 378/20; 378/15
[58] Field of Search .............. 364/413.15, 413.21; 378/20, 15

[56] References Cited

U.S. PATENT DOCUMENTS

| | | | |
|---|---|---|---|
| 4,426,715 | 1/1984 | Baer et al. | 378/4 |
| 4,630,202 | 12/1986 | Mori | 364/414 |
| 4,789,929 | 12/1988 | Nishimura et al. | 364/413 |
| 4,899,283 | 2/1990 | Annis | 364/413.15 |

*Primary Examiner*—Jerry Smith
*Assistant Examiner*—Russell E. Cass
*Attorney, Agent, or Firm*—Quarles & Brady

[57] ABSTRACT

A method of reducing image artifacts in tomographic projection imaging systems where the projection data is acquired using continuous gantry motion and using a variable table velocity to transport the imaged object past the rotating gantry. The table velocity is decreased when the projections are being acquired near the slice plane and increased when the projections being acquired are further from the slice plane. The table position is coordinated with the acquisition of projections so that the middle projections of the tomographic projection set are acquired close to the slice plane and the beginning and end projections are acquired when the projections are taken furthest from the slice plane. Interpolation procedures are used to further reduce image artifacts resulting from the taking of projection data at points removed from the slice plane.

7 Claims, 6 Drawing Sheets

METHOD FOR REDUCING SKEW IMAGE ARTIFACTS IN HELICAL PROJECTION IMAGING

BACKGROUND OF THE INVENTION

This invention relates to computed tomography using helical scanning. More specifically, the invention relates to reducing "skew" image artifacts resulting from tomographic reconstructions of projection data acquired in a helical scan.

As used herein, computed tomography shall refer both to tomography using "transmission imaging" that is, detecting radiation transmitted through the body being imaged, and "emission imaging", detecting radiation emitted from the body being imaged, e.g., such as that being emitted by radio pharmaceutical isotopes.

In a transmission imaging computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array oriented within the imaging plane. The detector array is comprised of detector elements which each measure the intensity of transmitted radiation along a ray projected from the x-ray source to that particular detector element. The intensity of the transmitted radiation is dependent on the attenuation of the x-ray beam along that ray by the imaged object. The detector elements can be organized along an arc each to intercept x-rays from the x-ray source along a different ray of the fan beam.

The x-ray source and detector array may be rotated on a gantry within the imaging plane and around the imaged object so that the angle at which the fan beam intersects the imaged object may be changed. At each gantry angle, a projection is acquired comprised of the intensity signals from each of detector elements. The gantry is then rotated to a new angle and the process is repeated to collect a number of projections along a number of gantry angles to form a tomographic projection set.

The acquired tomographic projection sets are typically stored in numerical form for computer processing to "reconstruct" a slice image according to reconstruction algorithms known in the art. The reconstructed tomographic images may be displayed on a conventional CRT tube or may be converted to a film record by means of a computer controlled camera.

In so called "fourth generation" transmission tomography systems, the detector array remains fixed and is expanded arcwise around the imaged object to subtend 180 degrees plus the fan beam angle or more of arc. In such systems, only the x-ray source is rotated to acquire the tomographic projection set.

Emission computed tomography may be performed in a similar manner. Briefly, a set of detectors are again rotated around the imaged object within an imaging plane. The detectors receive radiation not from an external x-ray source, but rather from radioactive isotopes within the object itself. The radiation received by the detectors reveals the relative concentrations of the radioactive source within the object being imaged. The detector array receives a different projection as its position is moved to different angles with respect to the imaged object all within the imaging plane.

In either emission or transmission computed tomography the detector array may be rectilinear rather than arcuate. The portions of the tomographic system that rotate, whether x-ray source, detector, or both shall be termed the gantry.

A typical computed tomographic study entails the imaging of a series of slices of an imaged object with the slices displaced incrementally along the z-axis, which is perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate electrical power and signals to and from the gantry. The slip rings permit continuous rotation of the gantry. Henceforth, unless otherwise stated, it will be understood that the systems described herein are equipped with slip rings or the like and are capable of continuous gantry rotation.

The time required to acquire the tomographic data set is more difficult to reduce. Present CT scanners require on the order of two seconds to acquire the projection set for one slice. This scan time may be reduced by rotating the gantry at a higher speed, but a higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the constant rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Referring to FIGS. 2 and 3, the motion of the gantry for a constant z-axis scan and a helical scan, respectively, are depicted The vertical axis on both figures indicates the relative z-axis position of the imaged object with respect to the imaging plane of the tomographic system, and the horizontal axis of both charts shows the gantry rotational angle $\theta$. It will be understood that for constant gantry rotational speed, the horizontal axis also represents time.

Referring to FIG. 2, in a constant z-axis scan, each tomographic projection set may be acquired over 360° and accordingly the horizontal axis on each chart has been marked to indicate the start and end of adjacent tomographic projections sets intervals of 360°. The solid line on each chart indicates the relative position of the imaged object with respect to the imaging plane and is denoted the scan path. As indicated, the imaged object is held stationary so that the image plane aligns with a slice place, established with respect to the imaged object, when the projection set is acquired. After the tomographic projector set for a slice plane is acquired, the image object is moved to the next slice plane during a repositioning period.

This differs from the helical scan path shown in FIG. 3 where the z-axis position of the imaged object with respect to the imaging plane has a constant velocity during the acquisition of each tomographic projection set. Accordingly, the scan path is a sloped line. The slope of the scan path for helical scanning will be referred to as the scanning pitch.

Continuous translation of the imaged object during scanning shortens the total scanning time required for the acquisition of a given number of slices. Nevertheless, helical scanning as depicted in FIG. 3 introduces certain errors with regard to the data in the acquired projection sets. The mathematics of tomographic reconstruction assumes that the tomographic projection set is acquired along a constant z-axis slice plane, as indicated by the horizontal slice plane lines in FIG. 3. The helical scan path of FIG. 3 clearly deviates from the horizontal lines of the constant z axis slice planes.

Referring to FIG. 4 the chart of the helical scan path of FIG. 3 is shown as modified by mapping $\theta$ values of greater than 360° over corresponding $\theta$ values from 0 to 360° so as to emphasize the periodicity of the gantry motion in $\theta$. This representation will be termed a "superimposed" scan path representation.

The deviation of the helical scan path from the slice plane results in image artifacts in the reconstructed tomographic image. The severity of the image artifacts depends generally on the "helix offset", indicated as the difference between z arguments of the scanned data and the z axis value of the desired slice plane and shown in FIG. 4. The helix offset error for a given scan path depends on the value of $\theta$ and is shown in FIG. 4 for $\theta = \theta'$. The errors resulting from helical scanning will be referred to as "skew" errors.

Several methods have been used to reduce skew errors in helical scanning. A first approach disclosed in U.S. Pat. No. 4,630,202 issued Dec. 16, 1986, reduces the pitch of the helical scan and then averages the projection data of consecutive 360° tomographic projection sets. The effect is equivalent to using a detector array which has both a larger width along the z axis, and which travels more slowly along the z-axis, i.e. with a lesser helical pitch. Skew errors are reduced using this method, but at the expense of requiring additional scanning time as is necessitated by the lower helix pitch. Thus, this method reduces, to some extent, the advantages to be gained by helical scanning.

Skew errors at the ends of the tomographic projection set may be reduced in conjunction with this approach by changing the weighting of the last and first projections of the consecutive 360° tomographic projection sets in the "averaging" process to give greater weight to the projection closest to the slice plane.

A second approach disclosed in U.S. Pat. No. 4,789,929 issued Dec. 6, 1988, also applies weighing to the projections of combined, consecutive 360° tomographic projection sets, but the weighting is a function of the helical offset of each projection at the given $\theta$. This interpolation approach generally reduces skew image but is prone to errors if the density of the imaged object changes rapidly along the z direction.

SUMMARY OF THE INVENTION

The present invention relates to a method of reducing skew errors by varying the translational velocity of the imaged object during the acquisition of a tomographic projection set. A slice plane is identified at a position relative to the imaged object and the imaged object is translated along the z-axis to move the slice plane past the image plane. A tomographic projection set is acquired, during which time the table motion is varied so that the translational velocity of the imaged object is decreased during the period prior to the slice plane crossing the imaging plane and increased during the period subsequent to the slice plane crossing the imaging plane.

It is one object of the invention to reduce skew errors in helical scanning. The non-uniform object motion concentrates the projections acquired in each tomographic projection set at positions along the z-axis close to the slice plane. By decreasing the average distance between the position of the acquired projection and the slice plane, skew artifacts are reduced.

The timing of the start of the acquisition of the tomographic projection is coordinated with the table motion so that projections with the greatest distance from the slice plane are acquired at the beginning and end of the acquisition of the tomographic projection. Such positioning further reduces the effect of skew error on the resultant image.

It is a further object of the invention to maintain the improved acquisition time of each tomographic projection set resulting from helical scanning. The varying table motion permits the continuous acquisition of projections with continuous gantry rotation. The average velocity can be maintained at the same value as that used in conventional helical scanning, hence scan time need not be increased.

The projection data of each tomographic projection set is stored along with the z-axis position of each projection. Interpolation between successive projection sets may then be used to further reduce the skew errors.

It is one aspect of the invention that the accelerative forces on the imaged object may be easily limited. In one embodiment, the velocity of the imaged object is varied linearly with time, hence the acceleration is constant. In a second embodiment the velocity of the imaged object is varied sinusoidally with time. In both instances peak acceleration of the imaged object and hence force on the imaged object may be limited to a predetermined value.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
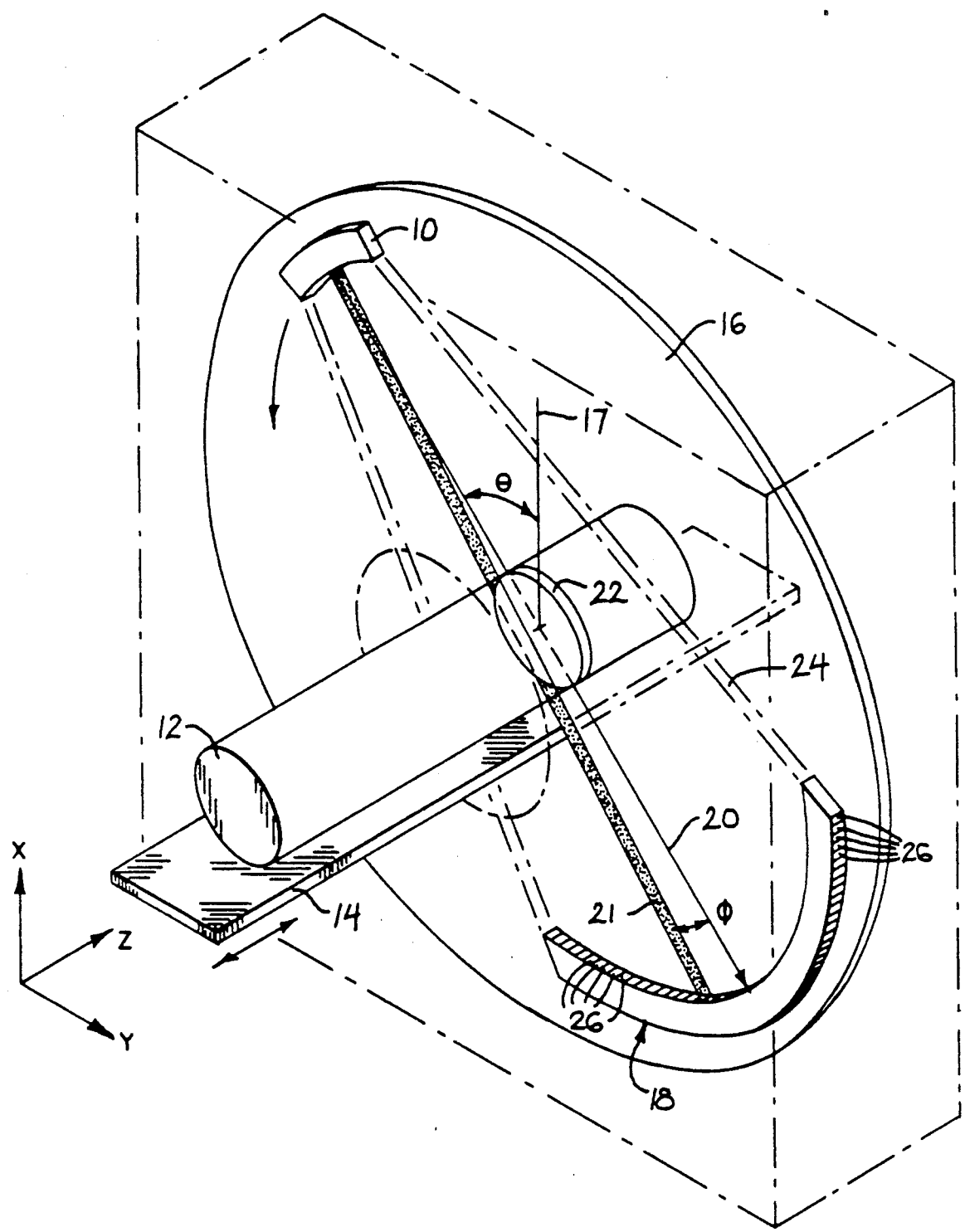
FIG. 1 is a pictorial representation of a CT gantry, table and imaged object suitable for use with the present invention showing the relative angles and axes associated therewith.
Figure 2:
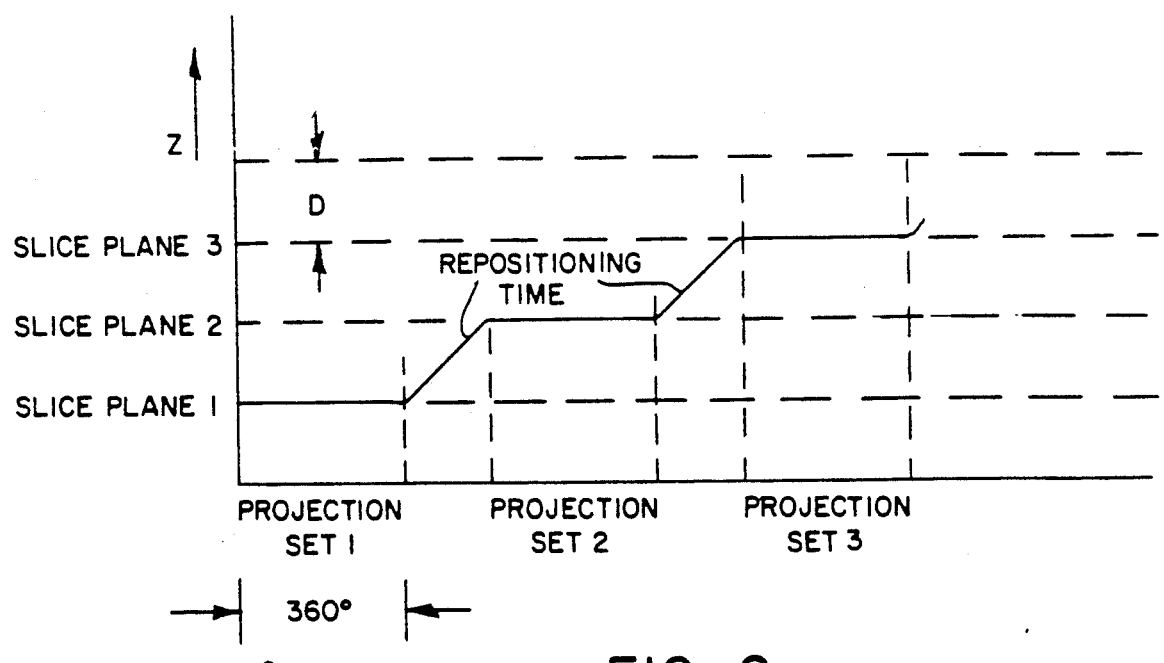
FIG. 2 is a graphic representation of the scan path of the system of FIG. 1 using constant z-axis scanning.
Figure 3:
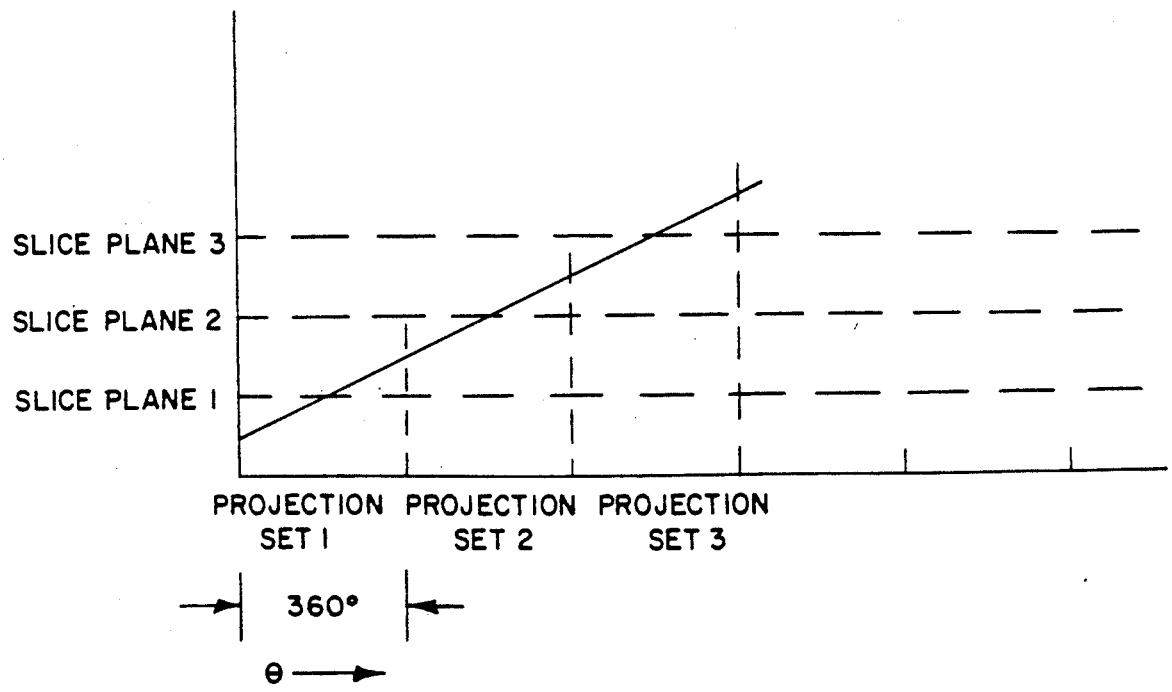
FIG. 3 is a graphic representation of the scan path of the system of FIG. 1 using helical scanning.
Figure 4:
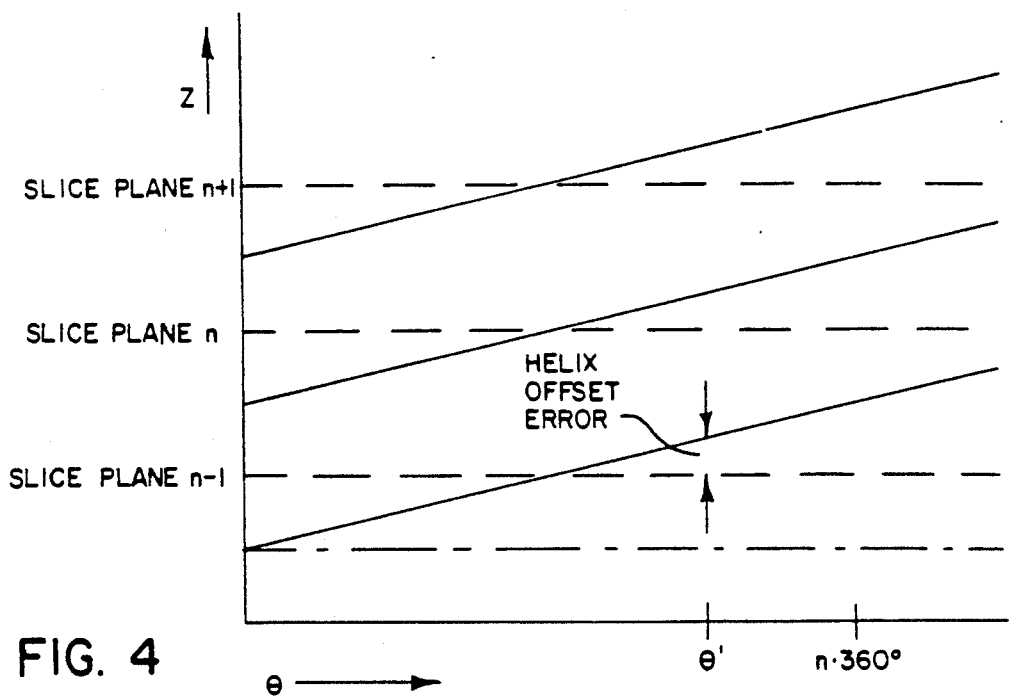
FIG. 4 is the graphic representation of FIG. 3 modified to superimpose $\theta$ values displaced by integer multiples of 360° and showing helix offset error.

Referring to FIG. 1, a CT gantry 16, representative of a "third generation" CT scanner includes an x-ray source 10 oriented to project a fan beam of x-rays 24 through imaged object 12 to detector array 18. The detector array 18 is comprised of a number of detector elements 26 which together detect a projected image resulting from the transmission of x-rays through the imaged object 12, or in the case of emission tomography, from the radiation emitted from the radio pharmaceutical isotopes within the imaged object 12. The angle $\phi$, measured from the centermost ray 20 of the fan beam 24, may identify each ray 21 of the fan beam 24 and its associated detector 26.

The angular position $\theta$ of the gantry 16 with respect to the imaged object 12 is arbitrarily referenced to zero when the fan beam's centermost ray 20 is vertical and directed downward. The gantry 16 is equipped with slip rings 50 (shown in FIG. 5), to be described below, which permit continuous gantry rotation without the need to stop and reverse the direction of the gantry 16 after a limited number of gantry rotations.

The imaged object 12 rests on table 14 which is radiotranslucent so as not to interfere with the imaging process. Table 14 may be controlled so that its upper surface translates along the z axis moving the imaged object 12 across the imaging plane swept by the fan beam 24.

Figure 5:
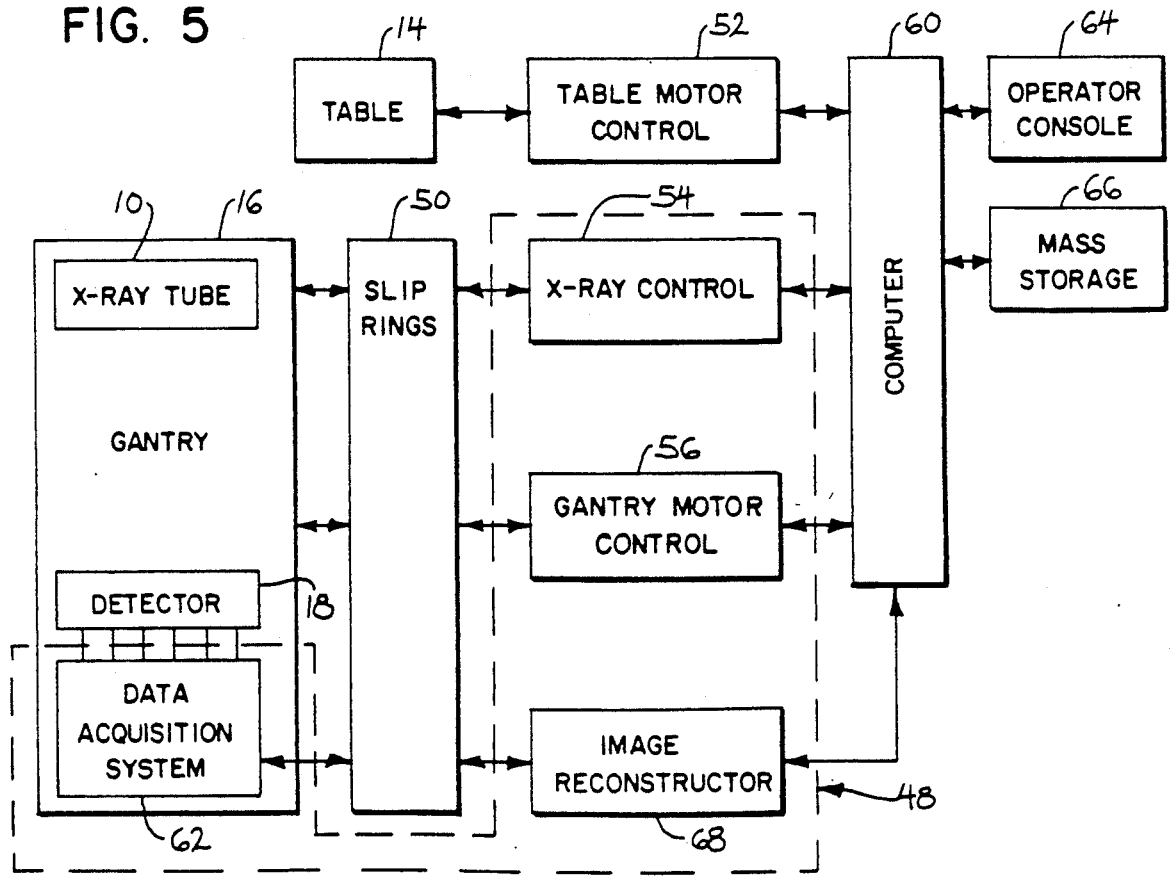
FIG. 5 is block diagram of a CT control system of the system of FIG. 1 and useful for practicing the present invention.

Referring now to FIG. 5, the control system of a CT imaging system suitable for use with the present invention has gantry associated control modules 48 which include: x-ray control 54 which provides power and timing signals to the x-ray source 10, gantry motor controller 56 which controls the rotational speed and position of the gantry 16 and provides information to computer 60 regarding gantry position, and image reconstructor 68 which receives sampled and digitized signals from the detector array 18 via the data acquisition system 62 to perform high speed image reconstruction according to methods known in the art. Each of the above can be connected to its associated elements on the gantry 16 via slip rings 50 and serves to interface computer 60 to various gantry functions.

The speed and position of table 14 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

A tomographic projection set must be acquired to produce a slice image. As discussed previously, the tomographic projection set is comprised preferably of projections acquired over 360° of gantry rotation. Each projection will contain x-ray intensity data from a number of detector elements 26 and is stored as a matrix of radiation intensity measurements $I(\theta_i, \theta_j)$ where i is an index number identifying the projection number within the tomographic projection set and j is an index number identifying the detector element in a given projection: $1 < j < D$, where D is the total number of detector elements. The value of the z-axis position of the imaged object 12 relative to the imaging plane is also stored in a variable $Z(\theta_i, \phi_j)$.

It will be assumed for the purposes of the following discussion that the gantry motion is at a constant angular velocity $\omega$ and that each projection of the tomographic projection set is evenly spaced in time. Nevertheless, it will be apparent to one skilled in the art, that the following embodiments may be readily modified for use with non-constant velocity gantry motions and projection acquisitions that are spaced unevenly in time.

Figure 6A:
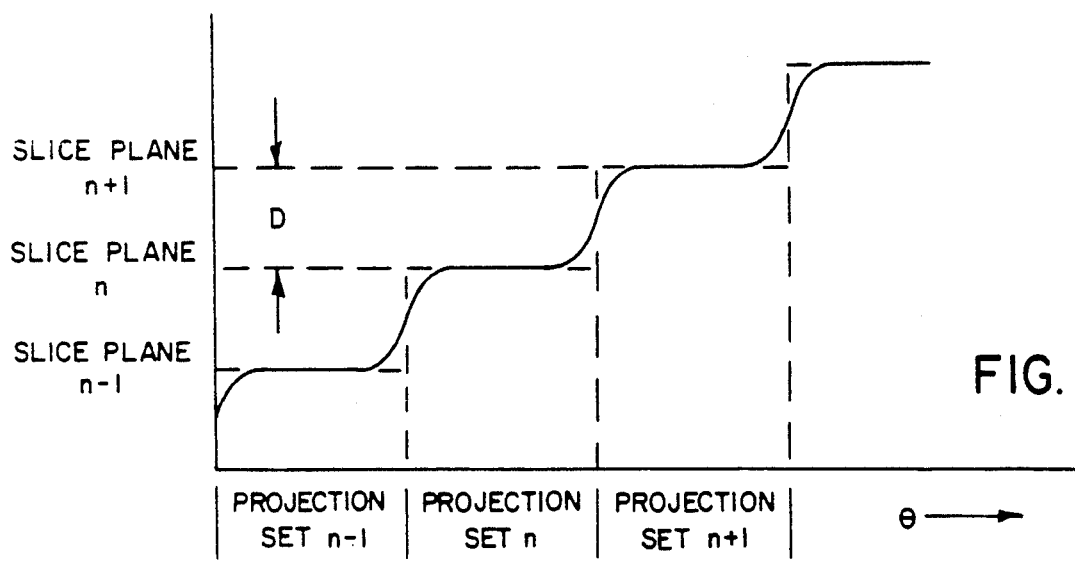
FIG. 6(a) is a graphic representation of the scan path of a helical scanning tomographic system according to a first embodiment of the present invention.

Referring to FIG. 6(a), a tomographic projection set "n" is acquired for z-axis positions around the slice plane "n". The projection set "n" is neither the first nor last tomographic projection set of the series acquired. The first and last tomographic projection sets are acquired in a different manner and will be discussed separately below.

In a first embodiment, the table speed is decreased, as indicated by the slope of the scan path in FIG. 6(a), at the beginning projections of tomographic projection set "n" to bring the imaging plane into alignment with the slice plane "n". At gantry angles corresponding to the acquisition of the middle projections of the tomographic projection set, the speed of the table 14 has been reduced to its lowest point to concentrate the projection data at z positions close to the slice plane "n". Near the end of the acquisition of the tomographic projection set, the table velocity is increased to bring the next slice plane "n+1" rapidly into alignment with the imaging plane.

The exact functional relationship between the projection number within the tomographic projection set and the table motion z is best understood by referring to the acceleration curve of the table 14. As shown by the chart in FIG. 6(c), the acceleration of the table 14 varies between one of three values: 0, $+a_m$, and $-a_m$. The magnitude of $a_m$ is determined by considering the maximum force of acceleration that is acceptably imposed on the imaged object 12. In the case of a human patient, this maximum force will be determined by balancing patient comfort and the desire to reduce patient motion with respect to the table 14, and the interest in faster scanning of the patient. As noted, faster scanning may favorably affect patient comfort to the extent that it reduces the time during which the patient must remain motionless.

A negative acceleration $-a_m$ is applied to the table 14 for time $\Delta T$ at the beginning of the acquisition of the tomographic projection set. At time $\Delta T$ before the completion of the projection set, a positive acceleration $+a_m$ is applied to the table 14. The time $\Delta T$ may be determined as follows:

$$\Delta T = \sqrt{\frac{D}{+a_m}} \tag{1}$$

where D is the distance between slice planes.

Figure 6B:
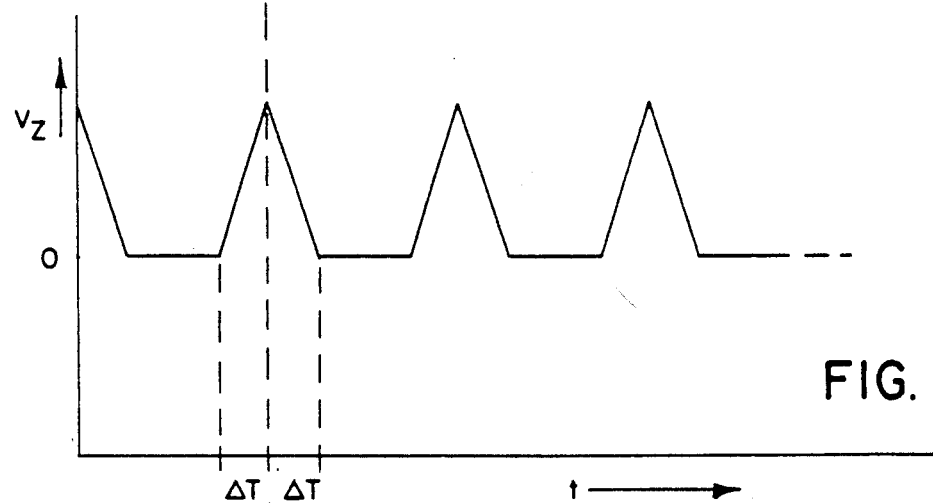
FIG. 6(b) is a graphic representation of the relative velocity between the imaging plane and the imaged object resulting in the scan path of FIG. 6(a)
Figure 6C:
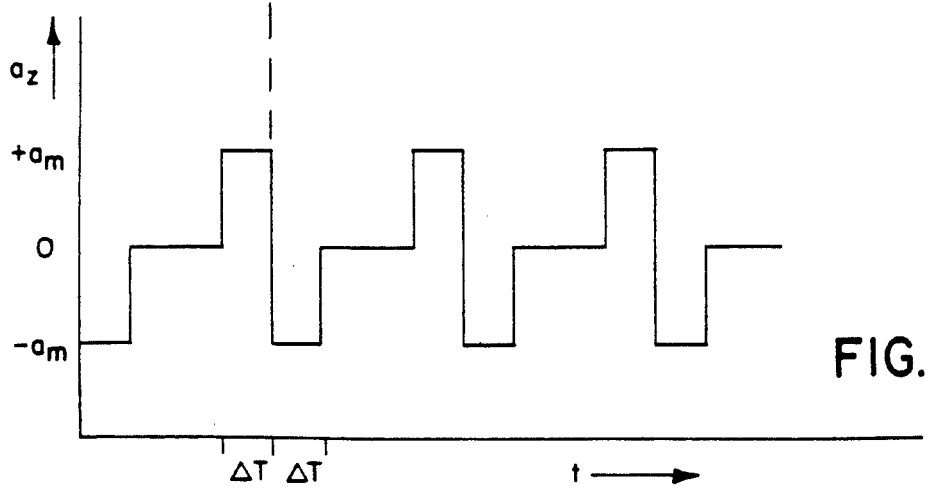
FIG. 6(c) is a graphic representation of the relative acceleration between the imaging plane and the imaged object resulting in the scan path of FIG. 6(a)

Referring to FIG. 6(b), the velocity of the table under alternating constant accelerations results in a triangular velocity plot centered at the beginnings and ends of each projection set. The average velocity of the table will be maintained at $D/\tau$ where $\tau$ is the time required to acquire a 360° tomographic projection set. Referring again to FIG. 6(a), the time during which the position of each slice plane is close to the imaging plane, has been increased. This reduces the average helical offset error.

Computer simulations have indicated that the image artifacts resulting from skew errors are further reduced if the projections, where the imaging plane is furthest from the scan plane are acquired at the beginning or end of the tomographic projection set. Accordingly, the gantry 16 and table 14 are pre-positioned so that the imaging plane crosses the slice plane at the time when the middle projections of the tomographic projection set are acquired.

Figure 7A:
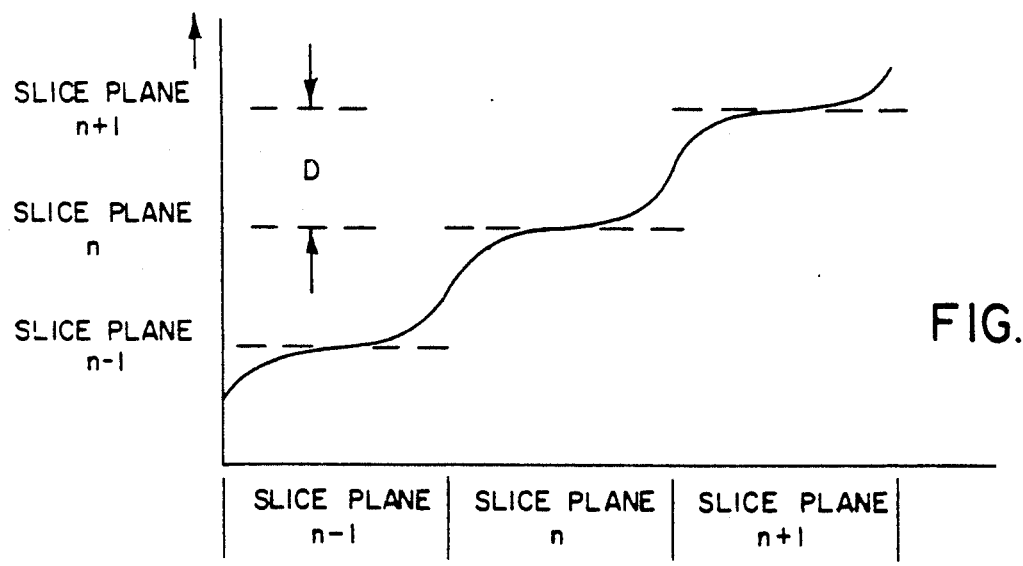
FIG. 7(a) is a graphic representation of the scan path of a helical scanning tomographic system according to a second embodiment of the present invention.

In a second embodiment, the table speed, as indicated by the slope of the scan path in FIG. 7(a), is also decreased at the beginning of the acquisition of the tomographic projection set "n" and increased at the end of the tomographic projection set. The functional relationship between the number of the projection within the tomographic projection set and the table position z is best illustrated by referring to the acceleration of the table 14 as shown in FIG. 7(c). The acceleration of the table 14 varies sinusoidally between $+a_m$ and $-a_m$ at a frequency equal to $1/\tau$ where $\tau$ is the time needed to acquire a 360° tomographic projection set and is equal to $2\pi/\omega$, where $\omega$ is the angular velocity of the gantry 16. The magnitude of $a_m$ is equal to $D/\tau$, the distance D between slice planes divided by the time needed to acquire a 360° tomographic projection set, as limited if necessary by the maximum acceptable force of acceleration on the imaged object 12. The value of $a_m$ for this embodiment may be somewhat higher than that for the previous embodiment because of the reduction in harmonic oscillation of the patient and table to be described further below.

Figure 7B:
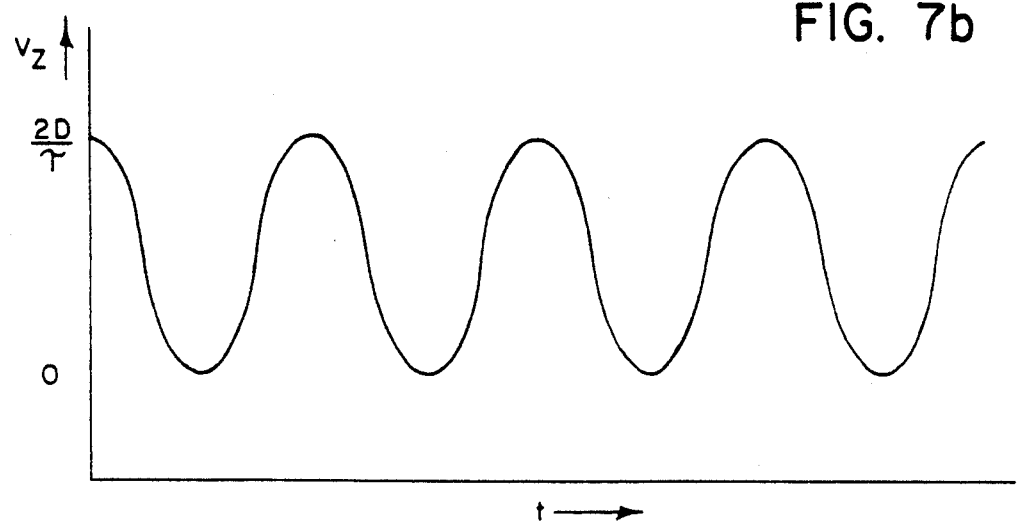
FIG. 7(b) is a graphic representation of the relative velocity between the imaging plane and the imaged object resulting in the scan path of FIG. 7(a)
Figure 7C:
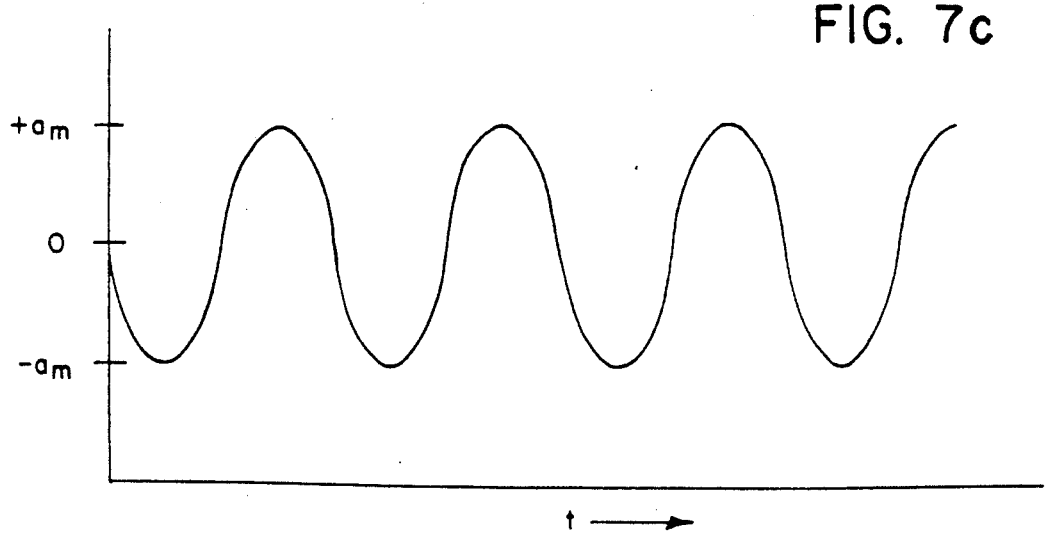
FIG. 7(c) is a graphic representation of the relative acceleration between the imaging plane and the imaged object resulting in the scan path of FIG. 7(a)

Referring to FIG. 7(b) the sinusoidal velocity, resulting from the acceleration shown in FIG. 7(c), is superimposed on a constant velocity component equal to $D/\tau$, the average velocity required to move from slice plane to slice plane in the time required to acquire one tomographic projection set. Accordingly, the velocity of the table 14 varies between $2D/\tau$ and 0. It should be noted that $D/\tau$ is the velocity of the table in conventional helical scanning, hence neither this embodiment of the invention nor the previous embodiment of the invention necessarily increases the total scanning time over that required in helical scanning with constant table motion.

Referring again to FIG. 7(a), the total time during which the position of the imaging plane is near a slice plane has been increased, which in turn will decrease helical offset errors. As with the previous embodiment, such errors are further reduced by acquiring those projections where the imaging plane is furthest from the slice plane, at the beginning and end of the tomographic projection set. The gantry 16 and table 14 are prepositioned so that the imaging plane crosses the slice plane during the acquisition of the middle projections of the tomographic projection set.

Referring again to FIG. 7(c), the acceleration acting on the imaged object 12 and hence the forces felt by the imaged object 12 are of a single frequency $1/\tau$. There may be advantages to such a driving function for the table 14 if mechanical resonances in the imaged object 12 and table 14, at frequencies other than $\omega$, are not excited into oscillation.

Figure 8B:
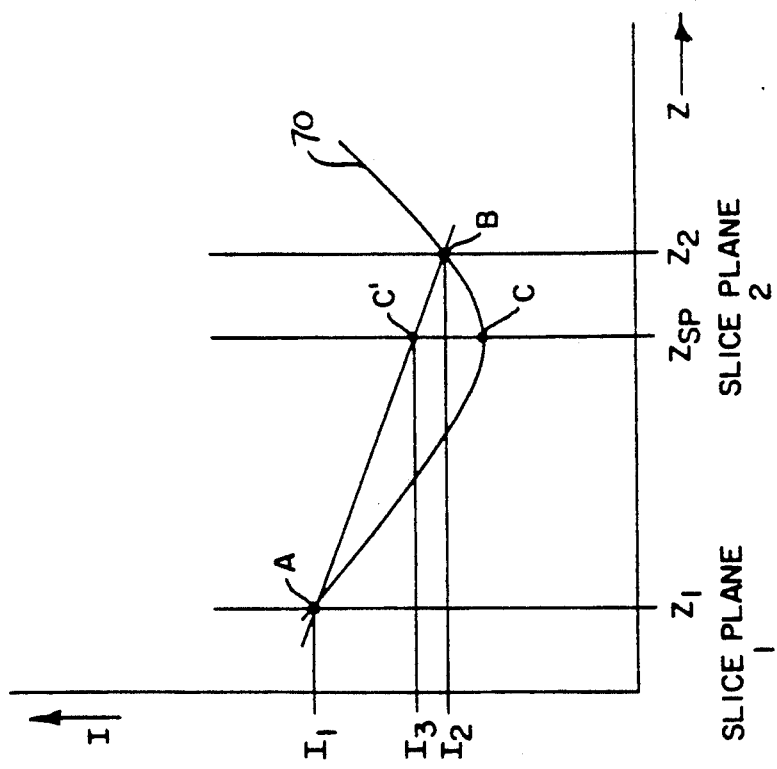
FIG. 8(b) is a graphic representation of the intensity values associated with one detector element of the projections identified in FIG. 8(a).
Figure 8A:
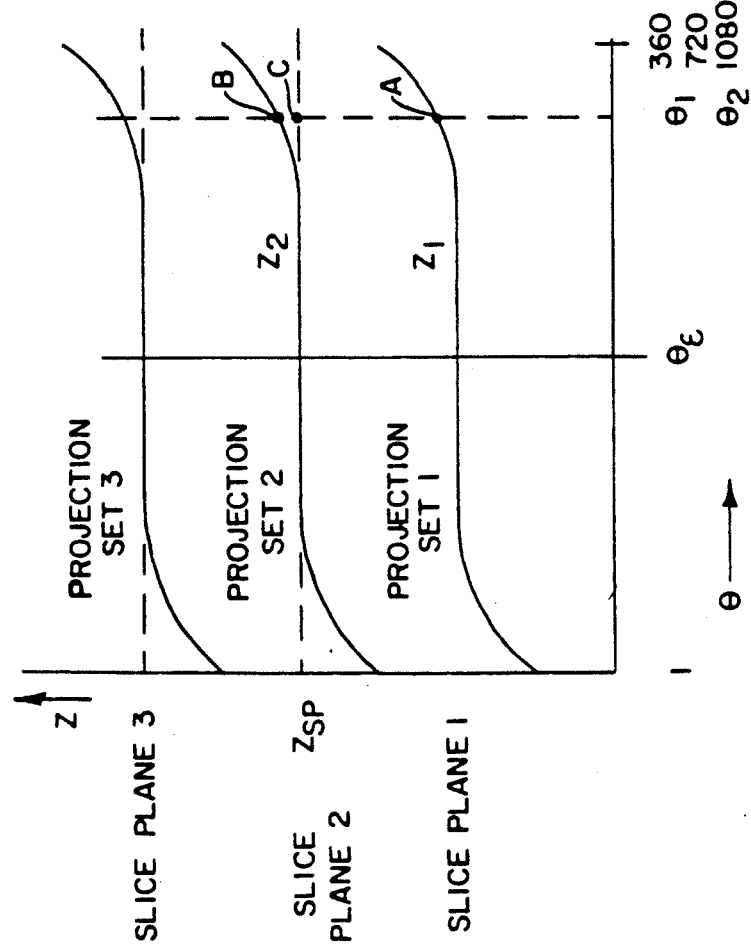
FIG. 8(a) is the graphic representation of FIG. 6(a) modified to superimpose $\theta$ values displaced by multiples of 360° and showing the selection of projections from adjacent tomographic projection sets for interpolation.

The data collected during a series of sequentially acquired tomographic projection sets may be interpolated to provide a more accurate representation of the data on the slice plane and to further reduce skew errors. Referring generally to FIGS. 8(a) and 8(b) the first step in the interpolation process is the identification of the z-axis value of the desired slice plane, referred to as $z_{sp}$. The slice planes are determined by the CT operator based on the approximate location of the internal structures of interest within the imaged object 12 and are fixed in position relative to the imaged object 12. FIG. 8(a) shows the scan path of the first embodiment with superimposed $\theta$ values, the slice plane $z_{sp}$ indicated as a horizontal dashed line.

A two point linear interpolation may be performed by determining, for each projection angle $\theta'$, (not shown) the tomographic projection sets closest to the slice plane $z_{sp}$ for arguments $\theta$ differing from $\theta'$ by an integer multiple of 360°. For slice plane $z_{sp}$, shown in FIG. 8(a), tomographic projection sets 2 and 3 are closest for projection angles $\theta_e$ and less, and projection sets 1 and 2 are closest to scan plane $z_{sp}$ for projection angles $\theta_e$ and larger.

As discussed previously, each projection of each tomographic projection set is comprised of elements I which are the signal values of single detector elements 26 at a particular gantry 16 position. For each element $I_1$ in projection set 1, and $I_2$ in projection set 2, the values of $I_1$ and $I_2$ are combined according to the following formula to create a new projection set $I_{int}$ such that:

$$I_{int} = wI_1 + (1-w)I_2 \quad (2)$$

where w is a weighting function with a value between 0 and 1 which weights $I_1$ and $I_2$ according to the distance they were acquired from the slice plane $z_{sp}$. For example, for a two point linear interpolation between data elements $I_1(\theta i_1, \phi_j)$ at $z_1$ and $I_2(\theta i_2, \phi_j)$ at $z_2$ where $\theta i_2 = (n.360°) + \theta i_1$ for n = 1,2,3 ... then $$I_3(\theta_{i3}, \phi_j) = I_1(\theta_{i1}, \phi_j) \cdot \frac{(z_{sp} - z_2)}{(z_1 - z_2)} + I_2(\theta_{i2}, \phi_j) \cdot \frac{(z_1 - z_{sp})}{(z_1 - z_2)} \quad (3)$$

Referring to FIG. 8(b), a graphical interpretation of a two point linear interpolation is shown. The position of points A and B are plotted by intensity value along the z-axis for an arbitrary $\phi$. The interpolation process produces point C' at the imaging plane $z_{sp}$ removed from the actual intensity value of C that would be obtained if a projection had been actually acquired at $z_{sp}$. Point C lies on the plot of actual intensity values 70 of the imaged object 12. The difference in intensity between C' and C is the helical offset error remaining after linear interpolation. Generally, if the values of $z_1$ and $z_2$ are moved closer to zsp, as is accomplished by the non uniform table motion of the present invention, the remaining helical offset error is further reduced.

It will be apparent to one skilled in the art that higher order interpolation methods involving additional points from previous and subsequent helically acquired tomographic projection sets may be used to determine the value of point C including polynominal interpolations with two or more points.

Upon completion of the interpolation, the interpolated data set $I_3(\theta i_3, \phi_j)$ may be reconstructed according to reconstruction algorithms, such as filtered back projection, as is known in the art.

In both of these embodiments, the first and last tomographic projection sets of the slice series (not shown) are treated differently. For the first projection set, the slice plane is pre-positioned at the imaging plane and maintained in that position for a full 360° of gantry motion. For the last projection set, once the slice plane is brought into alignment with the image plane the table motion is stopped and again a full 360° of projection data is acquired. The reason for this different treatment of the first and last projection set is that there is no reason to advance the table from or to a slice plane where no projection data will be acquired.

It will be understood from the foregoing discussion that a lesser reduction in skew error will occur even without the above described interpolation step. If interpolation is not used, the first and last projection set may be limited to a total of 360° of projection data including that taken while the imaged object is moving to or from the first or last slice plane.

As mentioned, generally the interpolation error will vary in proportion to the helix offset error being corrected. A reduction in the total helix offset error distance, that is, the total distance between the scan path and the slice plane, will reduce the interpolation error. A reduction in the total helix offset error over the entire tomographic projection set may be realized through variable speed table translation as described above.

Many modifications and variations of the preferred embodiment which will still be within the spirit and scope of the invention will be apparent to those with ordinary skill in the art. For example, the projections used to perform the interpolation need not be on both sides of the slice plane, rather an extrapolation process may be used. Further, the reconstruction of the image from the tomographic projection data may be performed prior to the interpolation process as most reconstruction algorithms are essentially linear operations. Also, as mentioned, nonconstant gantry rotation and non-periodic projection acquisition times may also be combined with the present invention, with appropriate modifications to the table motions of these embodiments, as will be apparent to one skilled in the art. Further, it will be apparent that the foregoing invention may be combined with other imaging techniques including "half scan" and "underscan", the latter as disclosed in U.S. Patent application Ser. No. 4,580,219, issued Apr. 1, 1986 and entitled "Method for Reducing Image Artifacts due to Projection Measurement Inconsistencies", and incorporated herein by reference. A half scan technique is described in "Optimization of Short Scan Convolution Reconstruction in Fan Beam CT", Internal Workshop on Physics and Engineering in Medical Imaging, 1982, p.199. Both techniques apply reduced weighting factors to projection data acquired at the beginning and end of a scan.

What is claimed is:

1. A method of acquiring projection data on a tomographic imaging system including a means for acquiring a series of projections of an imaged object within an imaging plane at a plurality of angles about a z axis, and a table for translating the imaged object along said z axis with respect to the imaging plane, comprising the steps of:

identifying a slice plane at a position relative to the imaged object;
   translating the table along the z-axis to move the slice plane through the imaging plane;
   acquiring a tomographic projection set comprised of a plurality of projections of the imaged object; and
   decreasing the translational velocity of the imaged object during a first period of the acquisition of the tomographic projection set prior to the slice plane crossing the imaging plane and increasing the translational velocity of the imaged object during a second period of acquisition of the tomographic projection set subsequent to the slice plane crossing the imaging plane.

2. The method of acquiring the projection data of claim 1 including the additional step of:

coordinating the position of the imaged object during the acquisition of the tomographic projection set so that the slice plane crosses the imaging plane during the acquisition of the tomographic projection set when one half of the projections of the tomographic projection set have been acquired.

3. The method of acquiring the projection data of claim 1 wherein the translational velocity is decreased linearly with respect to time during the first period and increased linearly with time during the second period.

4. The method of acquiring projection data of claim wherein the translational velocity is decreased linearly with respect to time during the beginning projections of the tomographic projection set and increased linearly with respect to time for the end projections of the tomographic projection set.

5. The method of acquiring projection data of claim wherein the translational velocity varies sinusoidally about a constant average velocity and where the period of the sinusoidal variation is equal to the time required to acquire a projection set.

6. The method of acquiring helical projection data of claim 5 wherein the translational velocity varies sinusoidally between 0 and 2v where v is equal to the distance between slices D divided by the time $\tau$ required to acquire the projection set for a slice, where the frequency of the translational velocity variation is equal to $1/\tau$, and where the velocity is zero when one half of the projections of the tomographic projection set have been acquired.

7. A method of acquiring projection intensity data $I(\theta_i, \phi_j)$ on a tomographic imaging system including a detector rotatable about a z axis to receive radiation along an imaging plane and a table for translating an imaged object along said z axis comprising the steps of:

identifying a slice plane at a z value $z_{sp}$ at a position relative to the imaged object;

translating the table along the z-axis to move the slice plane through the imaging plane;

acquiring a first tomographic projection set at a first set of z values comprised of intensity data $I_1(\theta i_1, \phi_j)$ of the imaged object;

decreasing the translational velocity of the imaged object during a first period of the acquisition of the tomographic projection set prior to the slice plane crossing the imaging plane and increasing the translational velocity of the imaged object during a second period of acquisition of the tomographic projection set subsequent to the slice plane crossing the imaging plane;

acquiring a second tomographic projection set at a second set of z values comprised of intensity data $I_2(\theta i_2, \phi_j)$ of the imaged object;

interpolating with respect to z a tomographic projection set of intensity data $I_3(\theta i_3, \phi_j)$ from $I_1(\theta i_1, \theta_j)$ and $I_2(\theta i_2, \theta_j)$ where the $\theta i_1$ and $\theta i_2$ differ by an integer multiple of 360°;

reconstructing the tomographic projection set $I_3$ to produce a tomographic image.

* * * * *

UNITED STATES PATENT AND TRADEMARK OFFICE
CERTIFICATE OF CORRECTION

PATENT NO. : 5,046,003

DATED : September 3, 1991

INVENTOR(S) : Carl R. Crawford

It is certified that error appears in the above-identified patent and that said Letters Patent is hereby corrected as shown below:

Col. 6, line 48, "$I(\theta_i, \theta_j)$" should be --$I(\theta_i, \phi_j)$--.

Col. 9, line 39, "zsp" should be --$Z_{sp}$--.

Signed and Sealed this

Nineteenth Day of January, 1993

Attest:

DOUGLAS B. COMER

*Attesting Officer*  *Acting Commissioner of Patents and Trademarks*